(12) United States Patent
May et al.

(10) Patent No.: US 10,539,522 B2
(45) Date of Patent: Jan. 21, 2020

(54) METHOD FOR ANALYSIS OF HYDROCARBONS IN WATER

(71) Applicants: The University of Western Australia, Nedlands, Western Australia (AU); Chevron U.S.A. Inc., San Ramon, CA (US)

(72) Inventors: Eric Freemantle May, Crawley (AU); Michael Leslie Johns, Crawley (AU); Matthew Roshan Joseph Carroll, Crawley (AU); Einar Orn Fridjonsson, Crawley (AU); Paul Louis Stanwix, Crawley (AU); Brendan Francis Graham, Crawley (AU); Christopher John Kalli, Herne Hill (AU); Paul Steven Hofman, Perth (AU)

(73) Assignees: The University of Western Australia, Crawley, Western Australia (AU); Chevron U.S.A. Inc., San Ramon, CA (US)

( * ) Notice: Subject to any disclaimer, the term of this patent is extended or adjusted under 35 U.S.C. 154(b) by 62 days.

(21) Appl. No.: 15/574,476

(22) PCT Filed: May 16, 2016

(86) PCT No.: PCT/AU2016/000167
§ 371 (c)(1),
(2) Date: Nov. 15, 2017

(87) PCT Pub. No.: WO2016/183612
PCT Pub. Date: Nov. 24, 2016

(65) Prior Publication Data
US 2018/0143148 A1    May 24, 2018

(30) Foreign Application Priority Data

May 15, 2015   (AU) .............................. 2015901772

(51) Int. Cl.
*G01N 24/08*     (2006.01)
*G01R 33/46*     (2006.01)
(Continued)

(52) U.S. Cl.
CPC ......... *G01N 24/08* (2013.01); *G01N 33/1833* (2013.01); *G01R 33/30* (2013.01); *G01R 33/46* (2013.01)

(58) Field of Classification Search
None
See application file for complete search history.

(56) References Cited

U.S. PATENT DOCUMENTS

| 4,866,983 A | 9/1989 | Vinegar |
| 9,551,807 B2 * | 1/2017 | Walsh ...................... G01V 3/32 |
| 2009/0004748 A1 | 1/2009 | Ganesan |

OTHER PUBLICATIONS

Bays, J. T. et al., 'A NMR-Based Carbon-Type Analysis of Diesel Fuel Blends from Various Sources', U.S. Department of Energy, PNNL-22472, May 2013, Title; Section 5.0, pp. 9-10; Tables A.2, A.4, A.6.

(Continued)

*Primary Examiner* — Jermele M Hollington
(74) *Attorney, Agent, or Firm* — Hunton Andrews Kurth LLP (57) ABSTRACT

A method for analysis of hydrocarbons in water, the method comprising the steps of: extracting the hydrocarbons from a water sample; introducing the extracted hydrocarbons to a solvent system; determining the relative concentrations of the hydrocarbons in the solvent system and at least one solvent in the solvent system by 1H NMR analysis, wherein the solvent system comprises at least one solvent with a 1H NMR signal distinguishable from a 1H NMR signal of the hydrocarbons.

15 Claims, 7 Drawing Sheets

(51) Int. Cl.
*G01N 33/18* (2006.01)
*G01R 33/30* (2006.01)

(56) References Cited

OTHER PUBLICATIONS

International Search Report and Written Opinion issued in PCT application No. PCT/AU2016/000167 dated Aug. 1, 2016.

* cited by examiner

METHOD FOR ANALYSIS OF HYDROCARBONS IN WATER

CROSS-REFERENCE TO RELATED APPLICATIONS

The present application is a National Stage Application of PCT/AU2016/000167, filed May 16, 2016, hereby incorporated by reference, which claims priority to Australian Application Number 2015901772, filed on May 15, 2015, and also hereby incorporated by reference.

FIELD OF THE INVENTION

The present invention relates to a method for analysis of hydrocarbons in water.

BACKGROUND ART

Optical spectroscopy is currently used for detecting oil or grease contamination in water. This requires a window that inevitably becomes dirty, limiting the period between which intervention into the instrument is required. Direct detection (measurement performed directly on the contaminated water) currently employs either droplet counting or UV detection. Droplet counting will detect only free oil in droplet form (i.e. not that dissolved into the water) whilst UV will only detect aromatic content of the oil (and thus to determine ppm oil contamination, an aromatic/aliphatic ratio must be assumed for the oil).

Indirect detection techniques employ a solvent (e.g. cyclohexane) to extract (and hence concentrate) the oil contamination in the water. This solvent can then be analysed using IR to determine the oil contamination level. The method however relies on complete separation of the solvent and the water—this is particularly difficult to ensure, particularly when the water contains dispersant/surfactant chemicals. The technique requires substantial manual handling in the form of liquid/liquid extraction. In addition, small amounts of residual water can significantly degrade the quality of the measurement.

The preceding discussion of the background art is intended to facilitate an understanding of the present invention only. It should be appreciated that the discussion is not an acknowledgement or admission that any of the material referred to was part of the common general knowledge in Australia as at the priority date of the application.

SUMMARY OF THE INVENTION

In accordance with the present invention, there is provided a method for analysis of hydrocarbons in water, the method comprising the steps of:
  solid phase extraction of the hydrocarbons from a water sample;
  elution of the extracted hydrocarbons with a solvent system; and
  comparing the relative intensities of at least one $^1$H NMR signal of the hydrocarbons and at least one $^1$H NMR signal of at least one solvent in the solvent system,
wherein the solvent system comprises at least two solvents, wherein the first solvent has a $^1$H NMR signal distinguishable from a $^1$H NMR signal of the hydrocarbons and the second solvent is aprotic and the solvent system contains a known amount of a proton-containing solvent.

It will be understood that the term $^1$H NMR refers to proton nuclear magnetic resonance, Preferably, the intensity of the at least one $^1$H NMR signal of the solvent in the solvent system is comparable to the intensity of the at least one $^1$H NMR signal of the hydrocarbons. The present invention enables a user to adjust the amount of proton-containing solvent in the solvent system to provide a $^1$H NMR signal that is comparable to the intensity of the at least one $^1$H NMR signal of the hydrocarbons, This enables accurate determination of hydrocarbon concentrations in water down to the ppm level.

Advantageously, the solvent system provides a reference $^1$H NMR signal which provides a self-calibrating measurement.

Advantageously, the method of the present invention can detect both dispersed and dissolved hydrocarbons at the ppm level.

The hydrocarbon may be provided in the form of an oil or a grease.

Preferably, there is no overlap between the $^1$H NMR signal of the at least one solvent in the solvent system and the $^1$H NMR signal of the at least one hydrocarbon.

In one form of the invention, the at least one $^1$H NMR signal of the hydrocarbons is the signal or signals attributable to aliphatic hydrogen atoms. The aliphatic hydrogen atoms may include those attributable to methyl hydrogen atoms and methylene hydrogen atoms.

In one form of the invention, the at least one $^1$H NMR signal of the hydrocarbons is the signal or signals attributable to aromatic hydrogen atoms.

In one form of the invention, the at least one $^1$H NMR signal of the hydrocarbons is the signal or signals attributable to both the aliphatic and the aromatic hydrogen atoms.

Preferably, the step of
  comparing the relative intensities of at least one $^1$H NMR signal of the hydrocarbons and at least one $^1$H NMR signal of at least one solvent in the solvent system,
  comprises conducting two or more measurements.

In accordance with the present invention, there is provided a method for analysis of hydrocarbons in water, the method comprising the steps of:
  solid phase extraction of the hydrocarbons from a water sample;
  elution of the hydrocarbons with a solvent system;
  comparing the relative intensities of at least one $^1$H NMR signal of the hydrocarbons in the solvent system and at least one $^1$H NMR signal of a solvent in the solvent system by $^1$H NMR analysis,
wherein the solvent system comprises at least three solvents, wherein the first solvent has a $^1$H NMR signal distinguishable from a $^1$H NMR signal of the hydrocarbons attributable to aliphatic hydrogen atoms, the second solvent is aprotic, and the third solvent has a $^1$H NMR signal distinguishable from a $^1$H NMR signal of the hydrocarbons attributable to aromatic hydrogen atoms and the solvent system contains a known amount of a proton-containing solvents.

Preferably, the step of
  comparing the relative intensities of at least one $^1$H NMR signal of the hydrocarbons in the solvent system and at least one $^1$H NMR signal of a solvent in the solvent system by $^1$H NMR analysis,
  comprises conducting two or more measurements.

Advantageously, conducting two or more measurements with internal standards such as chloroform and hexamethylsiloxane at different concentrations enables the aliphatic and aromatic components of the hydrocarbons to be determined.

Preferably, the at least one solvent has low solubility in water.

Preferably, the solvent system is retained as a liquid over all plausible operating conditions. Anticipated operating conditions may range from about 4° C. for sub-sea conditions up to about 50° C.

Proton-containing solvents may be selected from the group comprising chloroform, dichloromethane, silicone oils, hexadecane, alcohols, cyclohexane and silanes including tetramethyl silane and hexamethylsiloxane. It will be appreciated that the operating conditions may affect the choice of solvent. For example, dichloromethane may have a too low boiling point for use in ambient conditions, but may be appropriate for subsea conditions.

Aprotic solvents may be selected from the group comprising tetrachloroethylene (TCE), carbon tetrachloride, deuterated solvents and carbon disulphide.

It will be appreciated that the choice of solvent will be influenced by he nature of the hydrocarbons and the frequencies of the relevant $^1$H NMR signals.

The solvent system may comprise 0.001 to 99.999% v/v of a proton-containing solvent. The solvent system may comprise 0.01 to 99.99% v/v of a proton-containing solvent. The solvent system may comprise 0.1 to 99.9% v/v of a proton-containing solvent. The solvent system may comprise 0.1 to 99% v/v of a proton-containing solvent. The solvent system may comprise 0.1 to 90% v/v of a proton-containing solvent. The solvent system may comprise 0.1 to 50% v/v of a proton-containing solvent. The solvent system may comprise 0.1 to 10% v/v of a proton-containing solvent. The solvent system may comprise 0.1 to 5% v/v of a proton-containing solvent. The solvent system may comprise about 1% v/v of a proton-containing solvent.

Where the at least one $^1$H NMR signal of the hydrocarbons is the signal or signals attributable to aliphatic hydrogen atoms, the solvent system preferably comprises chloroform and tetrachloroethylene. The solvent system may comprise 0.001 to 99.999% v/v chloroform. Preferably, the solvent system comprises 0.01 to 99.99% v/v chloroform. More preferably, the solvent system comprises 0.1 to 99.9% v/v chloroform. More preferably, the solvent system comprises 1 to 99% v/v chloroform. More preferably, the solvent system comprises 1 to 90% v/v chloroform. More preferably, the solvent system comprises 1 to 50% v/v chloroform. More preferably, the solvent system comprises 1 to 10% v/v chloroform. More preferably, the solvent system comprises 1 to 5% v/v chloroform. More preferably, the solvent system comprises about 1% v/v chloroform.

It will be appreciated that the ratio of chloroform to tetrachloroethylene can vary depending on the amount of hydrocarbons in the water. The lower the hydrocarbon concentration, the less chloroform is required. Preferably, the intensity of the chloroform signal and the aliphatic hydrocarbon signals are comparable.

Where the at least one $^1$H NMR signal of the hydrocarbons is the signal or signals attributable to aromatic hydrogen atoms, the solvent system preferably comprises hexamethylsiloxane and tetrachloroethylene. The solvent system may comprise 0.001 to 99.999% v/v hexamethylsiloxane. Preferably, the solvent system comprises 0.01 to 99.99% v/v hexamethylsiloxane. More preferably, the solvent system comprises 0.1 to 99.9% v/v hexamethylsiloxane. More preferably, the solvent system comprises 0.1 to 99% v/v hexamethylsiloxane. More preferably, the solvent system comprises 0.1 to 90% v/v hexamethylsiloxane. More preferably, the solvent system comprises 0.1 to 50% v/v hexamethylsiloxane. More preferably, the solvent system comprises 0.1 to 10% v/v hexamethylsiloxane. More preferably, the solvent system comprises 0.1 to 5% v/v hexamethylsiloxane. More preferably, the solvent system comprises about 0.2% v/v hexamethylsiloxane.

Where the at least one $^1$H NMR signal of the hydrocarbons is the signal or signals attributable to aliphatic and aromatic hydrogen atoms, the solvent system preferably comprises chloroform, hexamethylsiloxane and tetrachloroethylene. The solvent system may comprise 0.001 to 99.999% v/v chloroform and hexamethylsiloxane in total. Preferably, the solvent system comprises 0.01 to 99.99% to v/v chloroform and hexamethylsiloxane in total. More preferably, the solvent system comprises 0.1 to 99.9% v/v chloroform and hexamethylsiloxane in total. More preferably, the solvent system comprises 0.1 to 99% v/v chloroform and hexamethylsiloxane in total. More preferably, the solvent system comprises 0.1 to 90% v/v chloroform and hexamethylsiloxane in total. More preferably, the solvent system comprises 0.1 to 50% v/v chloroform and hexamethylsiloxane in total. More preferably, the solvent system comprises 0.1 to 10% v/v chloroform and hexamethylsiloxane in total, More preferably, the solvent system comprises 0.1 to 5% v/v chloroform and hexamethylsiloxane in total. More preferably, the solvent system comprises about 1% v/v chloroform and hexamethylsiloxane in total.

In accordance with the present invention, there is provided a solvent system for use in the analysis of hydrocarbons in water wherein the method for analysis of hydrocarbons in water comprises the steps of:
  solid phase extraction of the hydrocarbons from a water sample;
  elution of the extracted hydrocarbons with a solvent syste
  comparing the relative intensities of at least one $^1$H NMR signal of the hydrocarbons and at least one $^1$H NMR signal of at least one solvent in the solvent system,
wherein the solvent system comprises at least two solvents, wherein the first solvent has a $^1$H NMR signal distinguishable from a $^1$H NMR signal of the hydrocarbons and the second solvent is aprotic and the solvent system contains a known amount of a proton-containing solvent.

The method of the present invention may be automated. In an embodiment of an automated system, a $^1$H NMR measurement is first taken directly of the sample. In case a non-zero reading is obtained the step of extracting the hydrocarbons from a water sample and introducing the extracted hydrocarbons to a solvent system can be omitted, and thus avoiding premature saturation of the solid phase extraction (SPE) cartridge due to a sample with a high concentration of hydrocarbons.

In accordance with the present invention, there is provided an automated method for analysis of hydrocarbons in water, the method comprising the steps of:
  solid phase extraction of the hydrocarbons from a water sample;
  washing the solid phase extractant;
  elution of the hydrocarbons from the solid phase extractant with a solvent system;
  comparing the relative intensities of at least one $^1$H NMR signal of the hydrocarbons in the solvent system and at least one $^1$H NMR signal of a solvent in the solvent system,
wherein the solvent system comprises at least two solvents, wherein the first solvent has a $^1$H NMR signal distinguishable from a $^1$H NMR signal of the hydrocarbons and the second solvent is aprotic and the solvent system contains a known amount of a proton-containing solvent.

Preferably the solvent system is stored in a solvent tank and the solvent system is returned to the solvent tank after $^1$H NMR analysis.

Preferably the solid phase extractant is washed with water from a water storage tank and the water is returned to the water storage tank after the washing step.

In accordance with the present invention, there is provided an automated method for analysis of hydrocarbons in water, the method comprising the steps of:
  solid phase extraction of the hydrocarbons from a water sample;
  washing the solid phase extractant;
  elution of the hydrocarbons from the solid phase extractant with a solvent system;
  comparing the relative intensities of at least one $^1$H NMR signal of the hydrocarbons in the solvent system and at least one $^1$H NMR signal of a solvent in the solvent system,
wherein the solvent system comprises at least two solvents, wherein the first solvent has a $^1$H NMR signal distinguishable from a $^1$H NMR signal of the hydrocarbons and the second solvent is aprotic and the solvent system contains a known amount of a proton-containing solvent, and
wherein the solvent system is stored in a solvent tank and the solvent system is returned to the solvent tank after $^1$H NMR analysis.

In accordance with the present invention, there is provided an automated method for analysis of hydrocarbons in water, the method comprising the steps of:
  solid phase extraction of the hydrocarbons from a water sample;
  washing the solid phase extractant with water;
  elution of the hydrocarbons from the solid phase extractant with a solvent system;
  comparing the relative intensities of at least one $^1$H NMR signal of the hydrocarbons in the solvent system and at least one $^1$H NMR signal of a solvent in the solvent system,
wherein the solvent system comprises at least two solvents, wherein the first solvent has a $^1$H NMR signal distinguishable from a $^1$H NMR signal of the hydrocarbons and the second solvent is aprotic and the solvent system contains a known amount of a proton-containing solvent, and
wherein the water is stored in a water tank and the water is returned to the water tank after washing the solid phase extractant.

In accordance with the present invention, there is provided an automated method for analysis of hydrocarbons in water, the method comprising the steps of:
  solid phase extraction of the hydrocarbons from a water sample;
  washing the solid phase extractant;
  elution of the hydrocarbons from the solid phase extractant with a solvent system;
  comparing the relative intensities of at least one $^1$H NMR signal of the hydrocarbons in the solvent system and at least one $^1$H NMR signal of a solvent in the solvent system,
wherein the solvent system comprises at least two solvents, wherein the first solvent has a $^1$H NMR signal distinguishable from a $^1$H NMR signal of the hydrocarbons and the second solvent is aprotic and the solvent system contains a known amount of a proton-containing solvent, and
wherein the solvent system is stored in a solvent tank and the solvent system is returned to the solvent tank after $^1$H NMR analysis, and
wherein the water is stored in a water tank and the water is returned to the water tank after washing the solid phase extractant.

BRIEF DESCRIPTION OF THE FIGURES

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

DETAILED DESCRIPTION OF THE PREFERRED EMBODIMENTS OF THE INVENTION

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness. None of the cited material or the information contained in that material should, however be understood to be common general knowledge.

Manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Features of the invention will now be discussed with reference to the following non-limiting description and examples.

In a general form, the invention relates to a method for analysis of hydrocarbons in water, the method comprising the steps of:
  extracting the hydrocarbons from a water sample;
  introducing the extracted hydrocarbons to a solvent system;
  determining the relative concentrations of the hydrocarbons in the solvent system and at least one solvent in the solvent system by $^1$H NMR analysis,
wherein the solvent system comprises at least one solvent with a NMR signal distinguishable from a $^1$H NMR signal of the hydrocarbons.

Solid-phase extraction involves the transfer of an analyte from a mobile (typically liquid) to a stationary (typically solid) phase (the sorbent). The target analyte can then be recovered in an alternative stronger solvent if required. By contrast with liquid-liquid extraction, SPE has several advantages including low solvent consumption, high recovery factors and more rapid processing. It is also more readily automated, attainment of equilibrium with respect to analyte recovery is more easily determined and hence it is considered generally more suitable for on-line application.

Reversed phase SPE, as is applied in the applicant's results, involves analyte retention as a result of weaker van-der-Waals forces acting between the analyte and the functional groups of the sorbent. As such, this relies more on the molecular structure of the analyte than on interactions between functional groups. This presents poor selectivity, which in the current application (detecting total hydrocarbon content in water) is advantageous as the analyte of interest is generally a range of hydrophobic compounds.

Typical sorbents for this non-specific retention of hydrocarbons are surface modified silicas, porous polymers and carbon. The most commonly used are chemically bonded silicas where hydrocarbon chains are attached to the silanol groups of the silica base. The most abundant petroleum hydrocarbons that can be present in produced water are aliphatics, BTEX compounds and phenols. In the current work, commercially available octadecyl bonded, endcapped silica SPE cartridges (the Maxi-Clean SPE 900 mg C18, Grace, Columbia Md., United States) were utilised. Calculations were performed to provide an estimate of the volumes required for the different steps described below.

The SPE cartridges had a nominal 45 mg retention capacity. For discharge water with a contamination level of 5 ppm (5 mg/L), a maximum of 9 L of contaminated water would need to be pumped through the cartridge before saturation is achieved. At 20 ppm (20 mg/L), 2.25 L of contaminated water would be needed for saturation. In practice it is prudent to operate significantly away from the saturation point and the feed of contaminated water was capped at 15 L.

The SPE cartridges were extensively tested for saturation, degradation and retention. No degradation of the cartridges was observed for the selected solvent and the saturation and retention capacities were consistently in accordance with the manufacturer's specifications. The results obtained indicated a greater tolerance for residual water contamination using the NMR device as opposed to a commercial Quantum Cascade Laser (QCL) device (Eralytics Eracheck)—for determination of oil contamination in water.

Conditioning of the SPE sorbent material was performed using ACS grade methanol bought from Sigma-Aldrich (Sigma-Aldrich, St.Louis, MO, United States) and deionized tap water. Conditioning was necessary to wet the sorbent material and activate the surface. Furthermore, it removed impurities present as a result of the manufacturing process.

Figure 1:
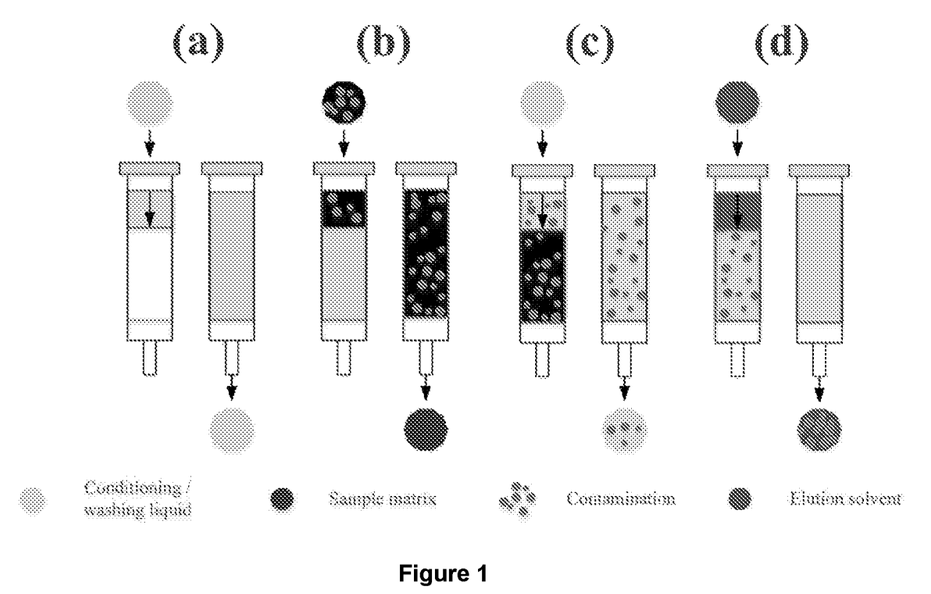
FIG. 1 shows a schematic of the basic SPE procedure with four steps (a) Conditioning (b) Loading (c) Washing and (d) Eluting.

Operation of the cartridges progressed through four distinct steps as follows and shown in FIG. 1:
  a) A conditioning step is composed of two sub-steps; the first activated the sorbent ligands, the second equilibrated the sorbent bed. For Reversed-Phase Extraction Procedure, conditioning consisted of rinsing with methanol followed by water.
  b) In the load step, a contaminated sample was applied to the SPE cartridge. The volume of the cartridge and the residence time of the contaminated sample in the cartridge must both be sufficiently large so as to quantitatively retain target analytes. The cartridge was processed at a flow rate of 1-5 mL/min.
  c) In the wash step, a solvent should be chosen that elutes impurities but allows the target analytes to be retained by the SPE cartridge. Often the second conditioning solvent is also suitable for use as a wash solvent. For the present purpose, water was used for the wash step. Note this can be the sample that has had its oil contamination removed in a previous measurement.
  d) The elution step ideally removes all target analytes from the cartridge with minimal solvent to maximize sensitivity. For the present purpose, chloroform, dichloromethane and tetrachloroethylene were all considered as solvents (this was performed prior to final selection of the solvent) and found to be suitable.

All of the potential solvents had a $^1$H NMR signal sufficiently different to aliphatic hydrocarbons or they had no $^1$H NMR signal as shown in Table 1 below.

TABLE 1

Properties of shortlisted solvents for the extraction, concentration and subsequent $^1$H NMR measurement of aliphatic hydrocarbons from discharge water.

| Solvent | $^1$H NMR signal (ppm) | Boiling Pont (° C.) | Boiling Point (° C.) | Solubility in Water (g/L) |
|---|---|---|---|---|
| Chloroform | 7.3 | 60.5 | −63 | 7.95 |
| Dichloromethane | 5.3 | 39.8 | −97 | 13.2 |
| Tetrachloroethylene | Nil | 121 | −22 | 0.2 |
| Silicone Oils | 0.1 | 140 | −55 | 0.00097 |
| Carbon Disulphide | nil | 46 | −111 | 2.85 |

Initial testing of the cartridges in terms of their retention of the hydrocarbon impurity proceeded by considering pure n-hexane and n-hexane dissolved in water to its saturation point.

$^1$H NMR testing of the solvents was conducted using a 1T Halbach array magnet corresponding to a $^1$H NMR frequency of 43 MHz. The solvents were mixed with various concentrations (0.25%, 1%, 2%, 5%, 10%, 25%, 50% & 75%) of a representative crude oil. The oil peak was expected at a chemical shift position between 0.6-1.1 ppm which does not overlap with the resonance positions of the various solvents (see Table 1 above), allowing clean, unambiguous differentiation of the oil and solvent NMR signals. Note that tetrachloroethylene and carbon disulphide present no $^1$H NMR signal.

The $^1$H NMR signal from the oil was plotted against the known oil concentration for each solvent and showed a strong linear relationship between signal and oil concentration ($R^2 > 0.998$).

A mixture of tetrachloroethylene and chloroform, in the ratio 99:1 (volume), was chosen as the final elution solvent. Advantageously, the chloroform signal provided a self-reference peak which did not swamp (i.e. was not significantly larger) than the oil signal being measured. Consequently the resultant measurement of oil content was effectively self-calibrating—the relative signal intensity of the eluted hydrocarbon to that of the chloroform is required as a dimensionless ratio—absolute measurements of the hydrocarbon signal are not required to be calibrated.

The $^1$H NMR hardware was an ultra-compact (8 kg) bench-top Halbach array magnet and a Kea spectrometer, both built by Magritek Ltd., New Zealand. It has a $^1$H resonance frequency of 43.36 MHz and accommodates 5 mm (outer diameter) NMR sample tubes. The 1 Tesla Halbach array magnet features sufficient magnetic field homogeneity such that chemical shift resolution of the solvent and the contaminant is readily achievable.

Two connection tubings were used: Chem-sure and Pharmed. Chem-sure provided long-term stability in the presence of tetrachloroethylene/chloroform and would ultimately be selected for any practical deployment, Polyether ether ketone (PEEK) Y-connectors and cartridge adaptors were used The valves were 2-way normally closed 304 stainless steel solenoid valves with direct plunger operation. Specifically they were model ES 2-3 from Process Systems. The valves allow the rest of the system to be isolated while the compressed air flows through the cartridge, The valves were controlled using LabView via a custom electronic switch box and National Instruments CompactDAQ and NI9263 module.

Custom software was developed in LabView to control and automate the measurement, The software is capable of controlling the pump and valves according to predefined routines, which are used to test the parameters of the system and perform the measurement. The software is integrated with the NMR spectrometer so that the entire process can be completely automated.

The pump was an Ismatec REGLO-ICC 4-channel pump, capable of maintaining a flow rate of between 1-5 mL/min.

Results with the apparatus were acquired for a range of samples, NMR acquisitions were simple pulse-acquire free induction decays (FID) followed by Fourier Transformation to provide the frequency spectrum. Analysis of the two peaks present was automated such that the areas of the solvent (chloroform content) and the oil contamination were reported.

For quantification purposes, the peak intensity I of each NMR resonance and the number of $^1$H nuclei contributing to that resonance peak N are directly proportional:

$$I_X = K_s N \qquad \text{Equation 1}$$

where $K_s$ is a spectrometer constant. Relative quantification of two resonance peaks can be readily performed without knowledge of $K_s$. In the present system, the NMR signal contains two distinct resonance peaks—one for the contaminant and one for the solvent. The molar amount of the contaminant compound ($m_x$) can be calculated based on the following equation:

$$m_X = m_{ref} \frac{N_{ref}}{N_X} \frac{A_X}{A_{ref}} \frac{M_X}{M_{ref}} \qquad \text{Equation 2}$$

$A_X$ and $A_{ref}$ correspond to the absolute integrated peak area of the contaminant and the (reference) solvent compounds respectively. $M_X$ and $M_{ref}$ are the molecular weights and $N_X$ and $N_{ref}$ are the number of protons per mole of the corresponding compounds respectively. The molar amount of solvent $m_{ref}$ is a known quantity. Thus via measurement of $A_X/A_{ref}$, it is possible to determine $m_x$ via application of equation 2 with no need for system calibration. With regard to quantification of crude oil contamination, equation 2 has to be modified as the number of protons per molecule is generally not known. The hydrogen index, which is defined as the amount of hydrogen in the respective compound relative to the amount in water, can be exploited to give:

$$m_X = \frac{A_X}{A_{ref}} \frac{HI_{ref}}{HI_X} V_{ref} \rho_X \qquad \text{Equation 3}$$

The hydrogen indices $HI_{ref}$ and $HI_X$ of the reference compound and the contaminant have to be calculated separately. If the number of protons per molecule is known (as is the case for our reference solvent), the HI can be determined according to:

$$HI_{ref} = \frac{\rho_{ref} N_{ref}}{M_{ref} * 0.111} \qquad \text{Equation 4}$$

whereas the hydrogen index of crude oil is approximated by:

$$HI_X = 9\rho_X(0.15 + 0.2(0.9-\rho_X)^2)$$  Equation 5

Herein, $\rho_{ref}$ and $\rho_X$ are the densities of the reference compound and contaminant respectively. As the density of the crude oil has not been determined in this work, a typical value for aliphatic crude oil is applied. Hence, in the work presented here, equation 2 is used for hexane contaminated water and equation 3 for crude oil contaminated water.

Figure 2:
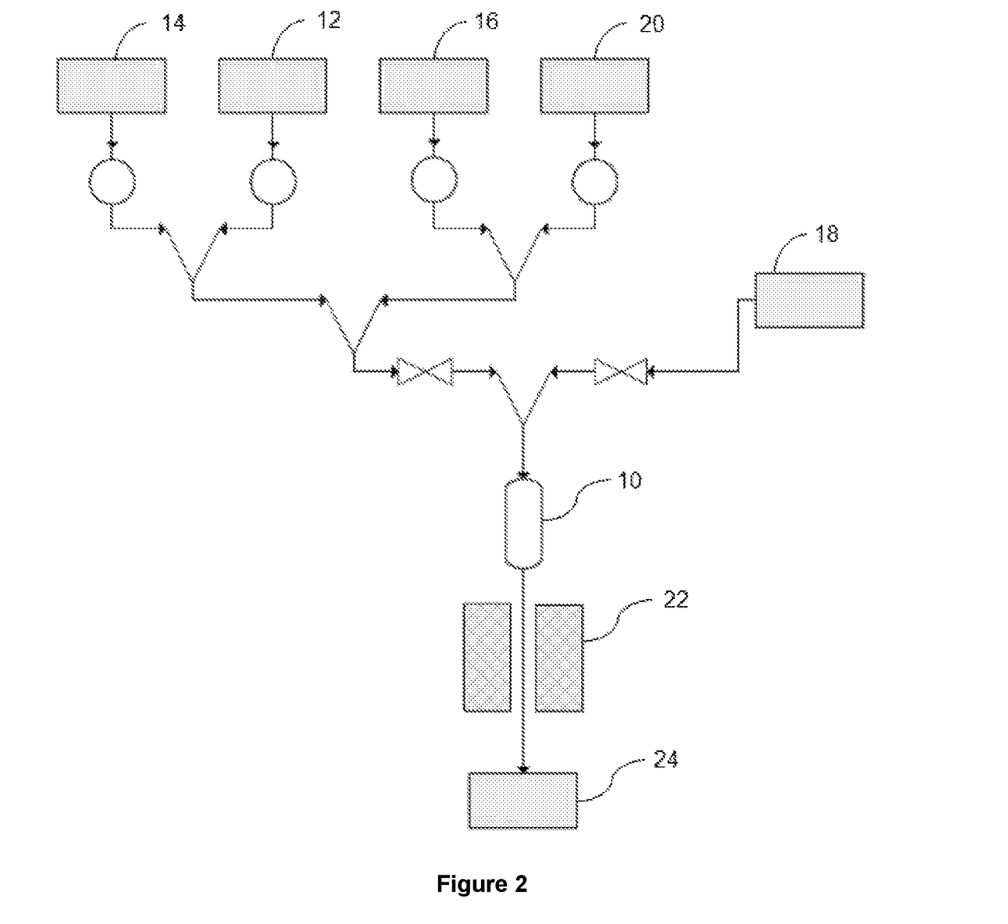
FIG. 2 shows a schematic representation of the automated system for analysis of discharge water.

A schematic for the automated system design is shown in FIG. 2. The steps in the process are:
 i. Preparation of cartridge 10 with conditioning solvent (methanol) 12 followed by DI water 14;
 ii. Run sample 16 for oil extraction;
 iii. Clear-out cartridge 10 by washing with DI water 14 followed by compressed air 18;
 iv. Run elution solvent (tetrachloroethylene/chloroform) 20 with continuous measurement by NMR 22; and
 v. Eluting sample 16 and elution solvent 20 to waste 24.

Figure 3:
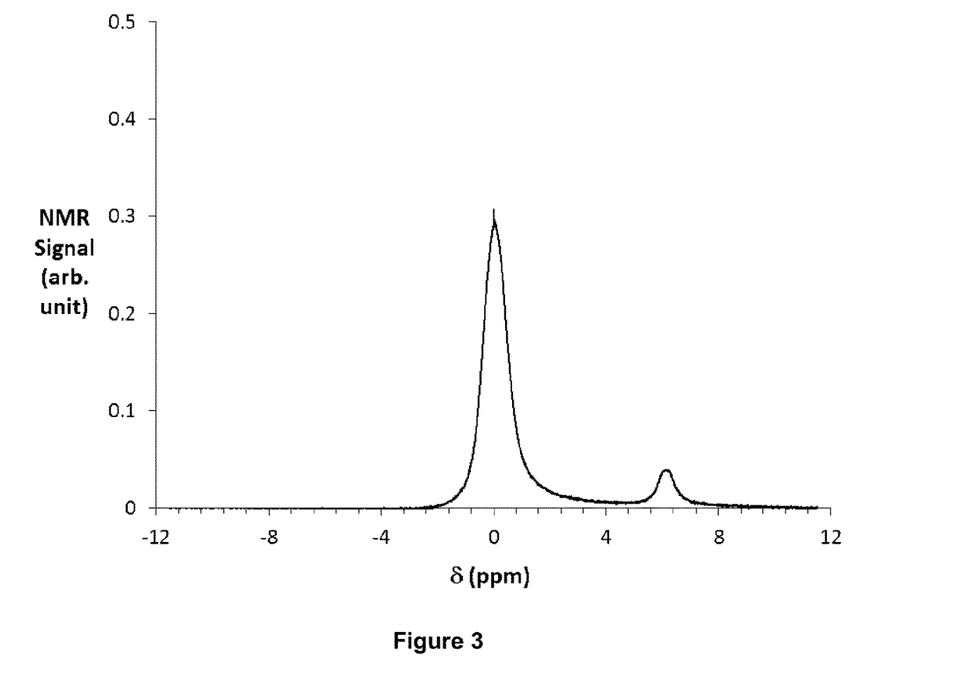
FIG. 3 is $^1$H frequency NMR measurements of the pure hexane sample after processing through the automated system. The small peak is from the 1% chloroform in the tetrachloroethylene solvent.

Examples of the resultant frequency spectrum are in FIG. 3. This corresponds to a pure hexane sample and provides a relatively quick test of the reliability and repeatability of the automated system. Knowing the amount of solvent used (5 mL) and the ratio of the solvent peak to hexane peak allowed for calculation of the amount of hexane that had eluted from the cartridge. For FIG. 3, this value was 35.2 mg and agreed with the stated SPE manufacturers total adsorption capacity.

The procedure was repeated a further 5 times, each with a separate cartridge (hence enabling variability between the cartridges to be explored). The results are shown in Table 2. These results were coupled with all pure hexane runs and resulted in a final average of 38.3±2.8 mg. Thus reasonable reproducibility was evident in terms of the total adsorption capacity of the cartridges. Note that knowledge of this total capacity is required to prevent early breakthrough of the contaminated water in the performance test conducted subsequently—it does not feature in the final calculation of water contamination at the ppm level described below.

TABLE 2

Results for the pure hexane samples, showing areas under the hexane and solvent peaks, the ratio between them and the calculated mass of hexane.

| Cartridge | Hexane area | Solvent area | Ratio | Hexane (mg) |
|---|---|---|---|---|
| 1 | 16.0 | 1.4 | 11.5 | 35.3 |
| 2 | 14.4 | 1.1 | 12.8 | 39.1 |
| 3 | 20.2 | 1.5 | 13.5 | 41.4 |
| 4 | 19.1 | 1.4 | 13.6 | 41.5 |
| 5 | 23.7 | 1.8 | 13.4 | 41.0 |

Figure 4:
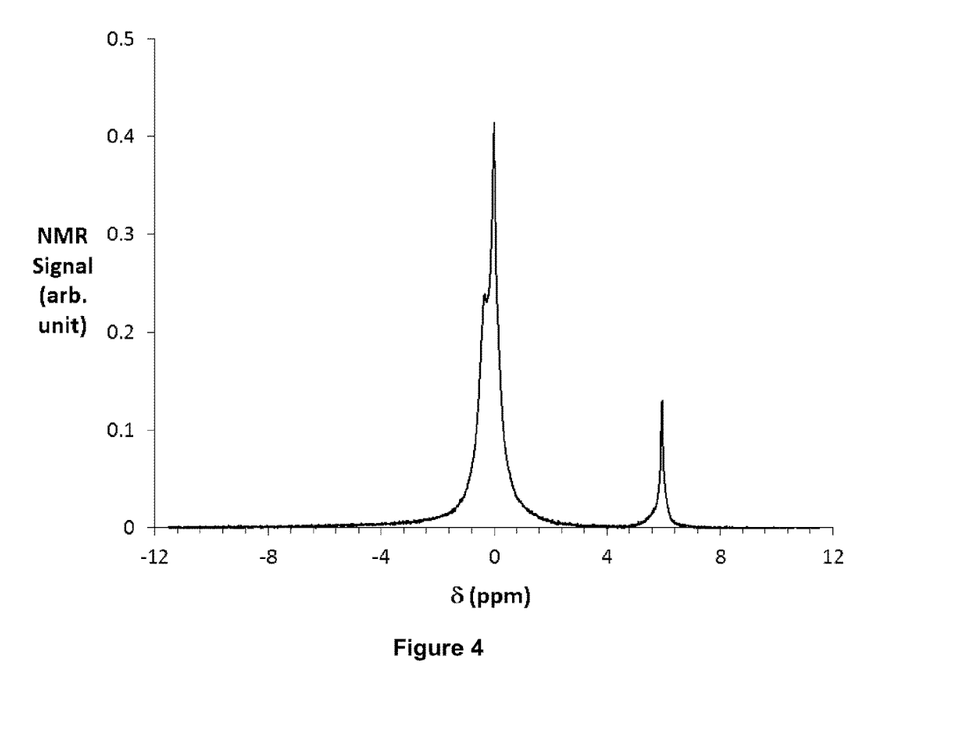
FIG. 4 is $^1$H frequency NMR measurements of the dilute hexane sample after processing through the automated system. The small peak is from the 1% chloroform in the tetrachloroethylene solvent.

The automated routine described above was implemented at 5 mL/min with 1 L of hexane contaminated water. A typical NMR spectrum for the dilute hexane sample is shown in FIG. 4.

The procedure was repeated 4 times, each with a separate cartridge. Each spectrum was analysed to determine the area under the hexane and solvent peaks. The ratio between the peaks was used to establish the mass of hexane that was eluted from the cartridge and this divided by the amount of dilute hexane solution (1 L) pumped through the cartridge. The results are shown in Table 3. These results show good repeatability for the procedure with a final average of 28.3±0.6 ppm.

TABLE 3

Results for the pure hexane samples, showing areas under the hexane and solvent peaks, the ratio between them and the calculated mass of hexane.

| Cartridge | Hexane area | Solvent area | Ratio | Hexane (ppm) |
|---|---|---|---|---|
| 1 | 44.2 | 4.9 | 9.0 | 28 |
| 2 | 46.1 | 4.8 | 9.6 | 29 |
| 3 | 46.6 | 5.0 | 9.3 | 28 |
| 4 | 46.7 | 5.0 | 9.3 | 28 |

Figure 5:
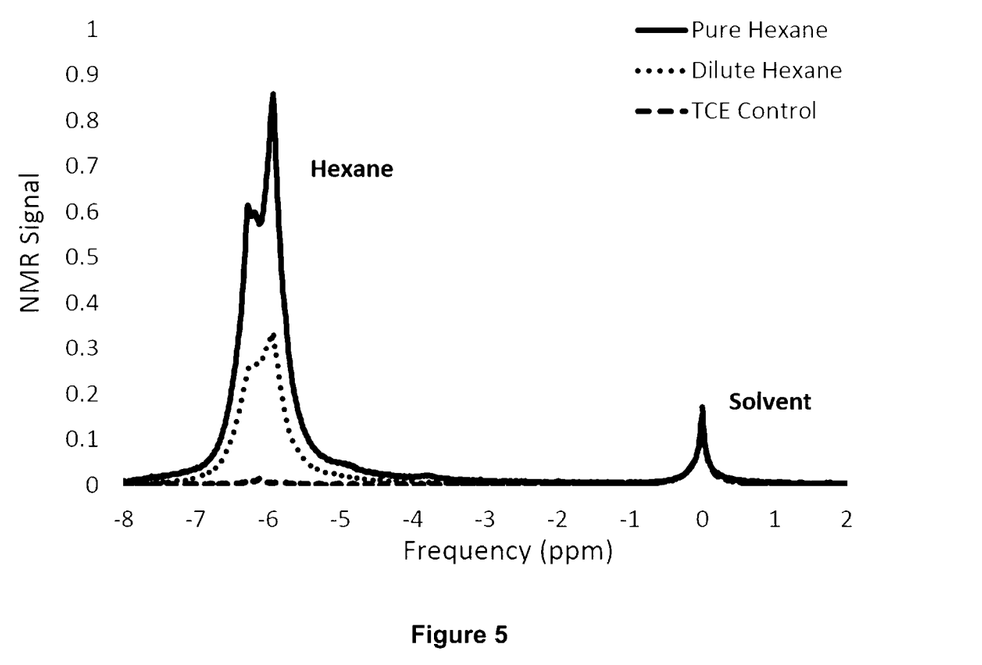
FIG. 5 shows a $^1$H NMR frequency spectrum of the 99% v/v tetrachloroethylene/1% v/v chloroform solvent solutions after being flushed through the solid phase extraction cartridges after no n-hexane, pure n-hexane and n-hexane dissolved in water have been flowed through the solid phase extraction cartridges.

FIG. 5 shows the resultant spectra detected by the NMR spectrometer for the original TCE/chloroform solvent and the solvents following elution for pure n-hexane and dilute n-hexane respectively. The ability to unambiguously distinguish the n-hexane and the solvent peaks is clear. In the case of pure n-hexane, analysis revealed that the maximum loading of the SPE cartridge was 11,577±459 ppm of n-hexane (following multiple repeats) which corresponded favourably with the SPE cartridge makers stated retention capacity of 11,250 ppm. For the saturated n-hexane water solution, 1.4 litres was flushed through the cartridge. Calculations of the original contamination of n-hexane resulted in a value of 14.4±0.4 ppm (multiple repeats) of dissolved n-hexane in water which compared favourably with literature (for which the range is 10-20 ppm). A subsequent repeat with the addition of 10 mg of free n-hexane to the solution resulted in a reading of 28.1 ppm which is consistent with an expected range of 20-30 ppm.

Contaminated water samples were prepared by homogenising an excess amount of hexane or crude oil in 2 L of water for two minutes. The samples were left overnight to equilibrate with an excess insoluble oil layer forming on the surface. This insoluble layer was retained throughout the measurements to minimise contaminant loss. Contaminated water was sampled from the bottom of the sample container. The cartridges were conditioned using 10 mL methanol followed by 10 mL of deionized water using the semi-automated apparatus.

Figure 6:
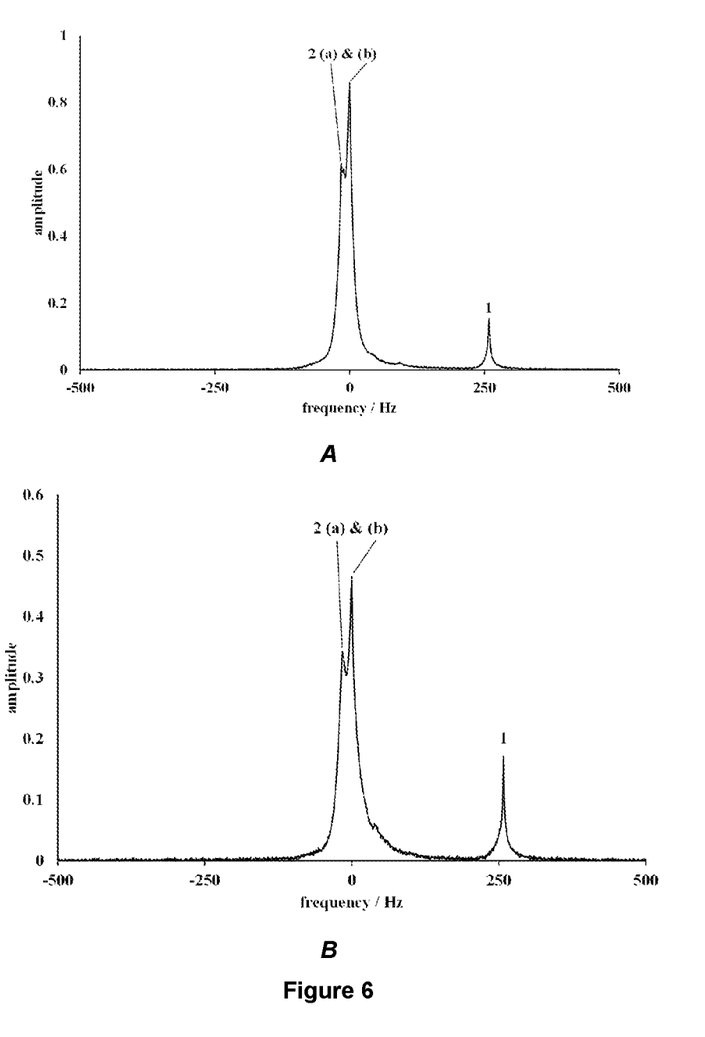
FIG. 6 shows sample spectra of (a) hexane and (b) crude oil in the 1% v/v $CHCl_3$ in TCE solvent. Peak 1 is the chloroform and peaks 2 (a) & (b) are the methyl and ethyl protons on the respective hydrocarbons.

Typical contamination spectra for hexane and crude oil in the solvent (at the upper limit of their intended concentration range) are shown in FIGS. 6(a) and 6(b) respectively. Separation of the hydrocarbon (peaks 2) and chloroform (peak 1) spectral features was excellent in both cases (the peaks for the crude oil are broader than those for hexane, consistent with its more heterogeneous composition) allowing automated area calculation for peaks 1 and 2 respectively.

Figure 7:
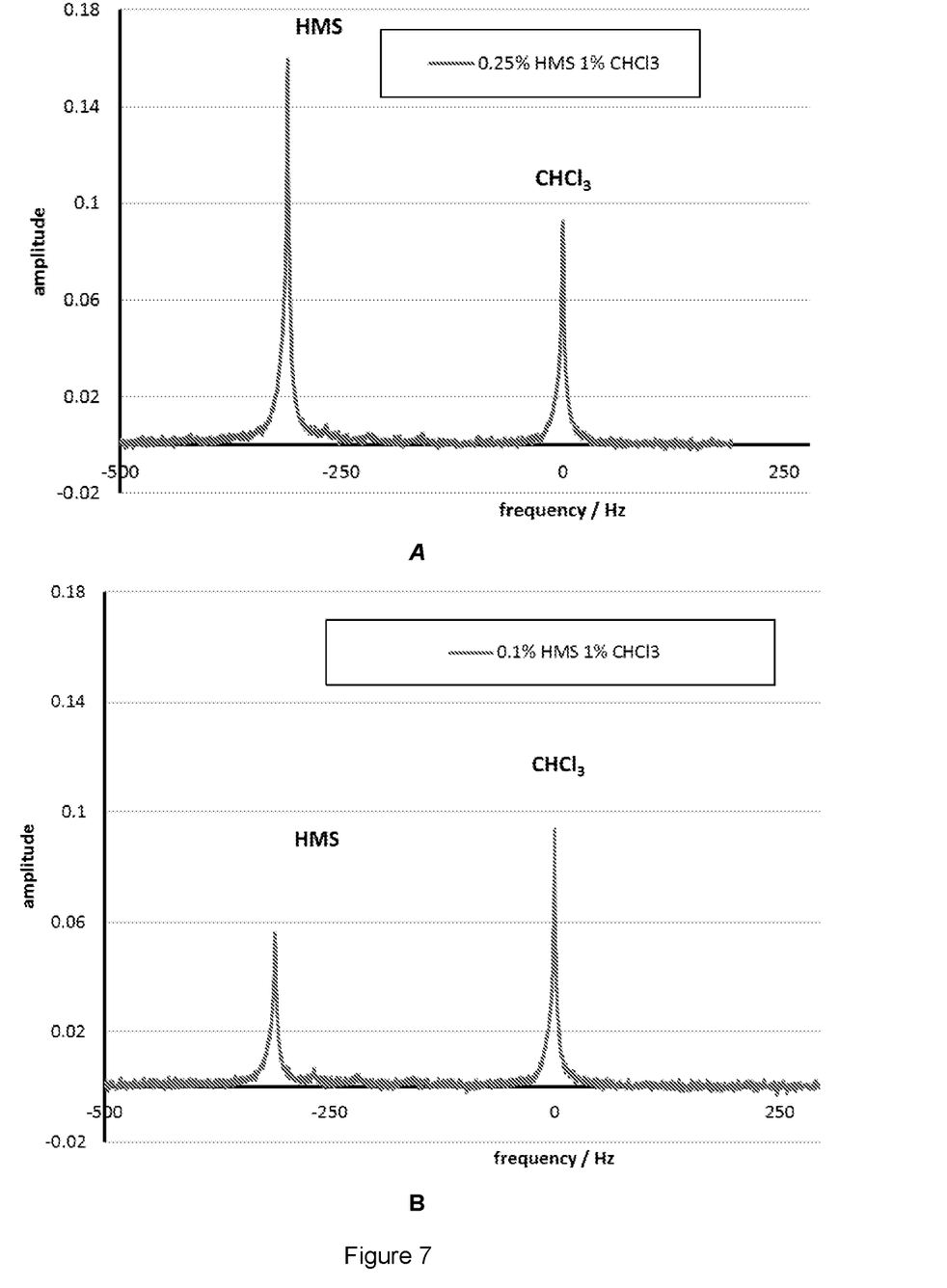
FIG. 7 shows $^1$H NMR spectra of two solvents (TCE) spiked with different ratios of $CHCl_3$ and hexamethylsiloxane (HMS) ((a) and (b)) and the resultant spectra when these solvents are individually applied to the SPE process (water sample contaminated with hexane and toluene) ((c) and (d)).

For the analysis of aromatics, the chemical-shift difference was adequate with an alternative solvent spike (e.g. 0.1 wt % cyclohexane in TCE or 0.2 wt % hexamethylsiloxane (HMS) in TCE), to reliably resolve the aromatic content at the ppm level. By applying both solvent spikes at the same time, it is possible to provide a unique self-calibrated measurement of both the amount of aromatics and the amount of aliphatics in the sample at the ppm level. This is most effectively done by taking two measurements using two solvents with both spikes present, but at a different ratio. Sample NMR spectra for these two solvents are shown below in FIG. 7(a) and (b) respectively—both spikes are evident and are labelled.

As an alternative method, the aliphatic content of a sample may be determined using chloroform in the solvent system followed by separate measurements with a solvent system comprising hexamethyl siloxane or cyclohexane, firstly without contamination and secondly with an contaminated water sample.

When applied individually to the SPE process, it is possible to simultaneously determine the ppm amount of aromatics (y) and aliphatics (x) in the sample by the change in the respective peak ratios for each solvent (two equations and two unknowns). This is shown below in FIG. 7(c) and (d) where the SPE process was applied to a water sample contaminated with both hexane and toluene. The measured hexane contamination (8±2 ppm) agreed extremely will with GC-FID validation measurements (8±3 ppm); the Toluene measurements (55±4 ppm) agreed reasonably well with the known amount added (~60 ppm).

To calculate concentrations from NMR data, two solvent ratios ($r_1=a_1/b_1$; $r_2=a_2/b_2$, where a and b are the solvent amounts) can be used to find the amount of aliphatics (x) and aromatics (y). Conducting two measurements we obtain $c_1$, $c_2$, $d_1$ and $d_2$, (c: aliphatic signal integral, d: aromatic signal integral) with subscripts (1) and (2) referring to measurements at different solvent ratios:

$$c_1 = a_1 + x \,\&\, c_2 = a_2 + x$$

$$d_1 = b_1 + y \,\&\, d_2 = b_2 + y$$

It is then possible to derive the following two equations to get the aromatics and aliphatics amounts:

$$y = d_2 - d_1 + \frac{(c_2 - c_1) - r_2(d_2 - d_1)}{r_2 - r_1}$$

$$x = c_1 - r_1 \frac{(c_2 - c_1) - r_2(d_2 - d_1)}{r_2 - r_1}$$

In summary, two measurements will be required to analyse a sample of contaminated water (using the different ratios of the respective solvent spikes) to determine both aliphatic and aromatic content.

The present invention affords the ability to determine the aliphatic and aromatic content of a sample either by separate measurements with different solvent systems or by a single solvent system at different concentrations.

An automated and continuous system that uses bench-top nuclear magnetic resonance (NMR) spectroscopy to detect oil or grease contamination in water has been developed. The first part of the system uses solid phase extraction methods to extract the oil/grease from the water. The second part of the system employs NMR spectroscopy for the detection and analysis of an appropriate eluting solvent. This is the first time that bench-top NMR has been used in a continuous process to detect oil contamination at the ppm level. The unique features of the system are the combination of the solid phase extraction with the NMR, and most importantly the type of solvent used. Together these features enable ppm levels to be accurately measured, In an unmanned, automated system, the solvent system could be reused. A small volume of solvent will be extracted from a large stock tank, analysed using the NMR, used to perform the solvent extraction and then reanalysed. It will then be returned to the stock tank. In this manner, replacement of the solvent tank will be required less frequently (obviously depending on size of tank, solvent amount used per extraction and frequency of measurement). It is estimated that a 100 L solvent tank with measurements performed every 30 minutes requiring 10 mL of solvent would last for 3-5 years, The benefits of this system are that it can detect oil contamination to levels below 1 ppm; it is self-calibrating against a comparable solvent signal (e.g. from chloroform, requiring comparative as opposed to absolute measurements; the system can better overcome small amounts of water presence in comparison to other commercial optical techniques; it is small in size, relatively inexpensive and can be automated or controlled remotely, making it ultimately suitable for sub-sea measurements.

The invention claimed is:

1. A method for analysis of hydrocarbons in water, the method comprising the steps of:
    solid phase extraction of the hydrocarbons from a water sample;
    elution of the extracted hydrocarbons with a solvent system; and
    comparing the relative intensities of at least one $^1$H NMR signal of the hydrocarbons and at least one $^1$H NMR signal of at least one solvent in the solvent system, wherein the solvent system comprises at least two solvents, wherein the first solvent has a $^1$H NMR signal distinguishable from a $^1$H NMR signal of the hydrocarbons and the second solvent is aprotic and the solvent system contains a known amount of a proton containing solvent, and
    wherein the solvent system provides a reference $^1$H NMR signal which facilitates a self-calibrating measurement.

2. A method for analysis of hydrocarbons in water according to claim 1, wherein the amount of proton containing solvent is controlled such that the intensity of the at least one $^1$H NMR signal of the solvent in the solvent system is comparable to the intensity of the at least one $^1$H NMR signal of the hydrocarbons.

3. A method for analysis of hydrocarbons in water according to claim 1, wherein the at least one $^1$H NMR signal of the hydrocarbons is the signal or signals attributable to aliphatic hydrogen atoms.

4. A method for analysis of hydrocarbons in water according to claim 1, wherein the at least one $^1$H NMR signal of the hydrocarbons is the signal or signals attributable to aromatic hydrogen atoms.

5. A method for analysis of hydrocarbons in water according to claim 1, wherein the at least one $^1$H NMR signal of the hydrocarbons is the signal or signals attributable to both the aliphatic and the aromatic hydrogen atoms.

6. A method for the analysis of hydrocarbons in water according to claim 1, wherein the solvent system comprises at least three solvents, wherein the first solvent has a $^1$H NMR signal distinguishable from a $^1$H NMR signal of the hydrocarbons attributable to aliphatic hydrogen atoms, the second solvent is aprotic and the third solvent has a $^1$H NMR signal distinguishable from a $^1$H NMR signal of the hydrocarbons attributable to aromatic hydrogen atoms and the solvent system contains a known amount of a proton-containing solvents.

7. A method for analysis of hydrocarbons in water according to claim 1, wherein comparing the relative intensities of at least one $^1$H NMR signal of the hydrocarbons and at least one $^1$H NMR signal of at least one solvent in the solvent system comprises conducting two or more measurements.

8. A method for analysis of hydrocarbons in water according to claim 1, wherein the proton-containing solvent is selected from the group comprising chloroform, dichloromethane, silicone oils, hexadecane, alcohols, cyclohexane and silanes including tetramethyl silane and hexamethylsiloxane.

9. A method for analysis of hydrocarbons in water according to claim 1, wherein the non proton-containing solvent is selected from the group comprising tetrachloroethylene, carbon tetrachloride, deuterated solvents and carbon disulphide.

10. A method for analysis of hydrocarbons in water according to claim 1, wherein the solvent system comprises chloroform and tetrachloroethylene.

11. A method for analysis of hydrocarbons in water according to claim 1, wherein the solvent system comprises hexamethylsiloxane and tetrachloroethylene.

12. A method for analysis of hydrocarbons in water according to claim 1, wherein the solvent system comprises chloroform, hexamethylsiloxane and tetrachloroethylene.

13. An automated method for analysis of hydrocarbons in water, the method comprising the steps of:
- solid phase extraction of the hydrocarbons from a water sample;
- washing the solid phase extractant;
- elution of the hydrocarbons from the solid phase extractant with a solvent system;
- comparing the relative intensities of at least one $^1$H NMR signal of the hydrocarbons in the solvent system and at least one $^1$H NMR signal of a solvent in the solvent system,
- wherein the solvent system comprises at least two solvents, wherein the first solvent has a $^1$H NMR signal distinguishable from a $^1$H NMR signal of the hydrocarbons and the second solvent is aprotic and the solvent system contains a known amount of a proton-containing solvent, and
- wherein the solvent system provides a reference $^1$H NMR signal which facilitates a self-calibrating measurement.

14. An automated method for analysis of hydrocarbons in water according to claim 13, wherein the solvent system is stored in a solvent tank and the solvent system is returned to the solvent tank after $^1$H NMR analysis.

15. An automated method for analysis of hydrocarbons in water according to claim 13, wherein the solid phase extractant is washed with water from a water storage tank and the water is returned to the water storage tank after the washing step.

* * * * *